United States Patent [19]

Obino et al.

[11] Patent Number: 5,800,498
[45] Date of Patent: Sep. 1, 1998

[54] CATHETER FOR IMPLANTABLE RHYTHM CONTROL DEVICE

[75] Inventors: Stanislao F. Obino, Edina; Paul J. Buscemi, Long Lake, both of Minn.

[73] Assignee: PharmaTarget, Inc., Maple Grove, Minn.

[21] Appl. No.: 639,131

[22] Filed: Apr. 26, 1996

[51] Int. Cl.⁶ ............................................. A61N 1/05
[52] U.S. Cl. ................................................. 607/123
[58] Field of Search ........................... 607/120, 121, 607/122, 123; 604/21, 323, 249, 236, 246

[56] References Cited

U.S. PATENT DOCUMENTS

| | | |
|---|---|---|
| 3,923,060 | 12/1975 | Ellinwood, Jr. . |
| 4,003,379 | 1/1977 | Ellinwood, Jr. . |
| 4,360,031 | 11/1982 | White . |
| 4,506,680 | 3/1985 | Stokes . |
| 4,577,642 | 3/1986 | Stokes . |
| 5,019,102 | 5/1991 | Hoene ............................ 604/323 |
| 5,081,990 | 1/1992 | Deletis . |
| 5,154,169 | 10/1992 | Miyata et al. . |
| 5,220,917 | 6/1993 | Cammilli et al. . |
| 5,433,742 | 7/1995 | Willis ............................ 607/122 |
| 5,447,533 | 9/1995 | Vachon et al. . |
| 5,476,501 | 12/1995 | Stewart et al. ................... 607/127 |

FOREIGN PATENT DOCUMENTS

37 35 137 A1   5/1989   Germany .

*Primary Examiner*—Scott Getzow
*Attorney, Agent, or Firm*—Merchant, Gould, Smith, Edell, Welter & Schmidt, P.A.

[57] ABSTRACT

A catheter for use with an implantable drug dispensing arrhythmia control device, includes a lumen and valve for dispensing the drug, and multiple electrodes for sensing heart activity.

10 Claims, 6 Drawing Sheets

CATHETER FOR IMPLANTABLE RHYTHM CONTROL DEVICE

TECHNICAL FIELD

The present invention relates generally to medical devices for implantation in the human body and more particularly to catheter structures for use with a device adapted for treating arrhythmias such as atrial or ventricular fibrillation of the heart.

BACKGROUND ART

Implantable drug pumps are known from Ellingwood, Jr. U.S. Pat. No. 4,003,379 and implantable pharmacological defibrillators are known from Camelli et al. U.S. Pat. No. 5,220,917. These references show that an implantable rhythm control device may be used for treating certain arrhythmias. However these references indicate a need for improved catheter structures for chronic use for treatment of certain disorders of the heart.

SUMMARY DISCLOSURE OF THE INVENTION

The present invention is disclosed in the context of an assembly of an implantable rhythm control device and a complimentary catheter. The rhythm control device includes several items. For example the rhythm control device will include a bio-compatible housing capable of being implanted in the human body. A drug reservoir and associated pump system will be positioned in the housing along with an energy source. Electronic circuitry for analyzing electrical signals produced by the heart and received from the catheter will be positioned in the housing as well. This circuitry will be used to evaluate the heart rhythm and to indicate the onset of an arrhythmia. It is also contemplated that electrical energy may be supplied to the heart through the catheter to treat induced bradycardia or other rhythm disturbances. In general the reservoir in the device the will supply or dispense the drug through an outlet opening in the catheter in response to a signal from the electronic circuitry indicating the onset of arrhythmia of the heart.

The catheter portion of the assembled system includes an elongate body that has a distal end and a proximal end. There is a fluid delivery lumen extending longitudinally along the axial length of the body from an inlet end at the proximal end to an outlet port spaced between the proximal end and a distal end of the body. There are at least first and second electrodes on the peripheral surface of the body that are connected by first and second electrical leads which extend longitudinally within the body to contact ends of the leads at the proximal end of the body. The first electrode is preferably at the distal end of the body and the second electrode is spaced longitudinally along its peripheral surface from its distal end to position the catheter in the right atrium or a major vein of the heart. A valve is located on the body at the outlet port of the lumen to permit delivery of the drug out the outlet port. This valve also prevents fluid from entering the outlet port.

Thus, when coupled to the catheter, the rhythm control device can receive and monitor electrical signals of the heart, supply a drug for treating the tissues of the heart and provide electrical energy to pace the heart. The number of and locations for electrodes can be varied. Preferably three electrodes are used, including a third electrode spaced from the first electrode to be in the right atrium of the heart when the first electrode is in the apex of its right ventricle and connected by a third lead with the electrical input connection so that the electronic means receives signals between the second and third electrodes to monitor activities in the right atrium chamber of the heart, and receives signals between the first electrode at its distal end and the housing to monitor activities in the right ventricle chamber of the heart. Four electrodes can also be used including the second and third electrodes positioned and connected as described above when three electrodes are used, and a fourth electrode spaced a distance from the first electrode to be in the right ventricle of the heart when the first electrode is in the apex of its right ventricle and connected by a fourth lead with the electrical input connection so that the electronic means receives signals between the second and third electrodes to monitor activities in the right atrium chamber of the heart, and between the first and fourth electrodes to monitor activities in the right ventricle chamber of the heart.

Preferably the outlet port opens through the peripheral surface of the body at a location that will be in the right atrium chamber of the heart when the first electrode is in the apex of its right ventricle. The valve at that outlet opening can comprise an enclosure of resiliently elastic material tensioned around and fixed along the peripheral surface over the outlet port and adapted to be resiliently flexed by pressure applied through liquid in the lumen to afford movement of liquid through that outlet port and between the peripheral surface and the enclosure.

The elongated body of the catheter can have a longitudinally extending stylet passageway that is adapted to receive a stylet for stiffening and shaping the catheter during its insertion into the body.

Furthermore, active or passive fixation structures such as screws or tines may be provided to the distal end of the catheter to engage with the tissues of the heart.

BRIEF DESCRIPTION OF DRAWING

An illustrative embodiment of the present invention will be further described with reference to the accompanying drawing wherein like reference numerals refer to like parts in the several views, and wherein.

DETAILED DESCRIPTION

Referring now to FIGS. 1 through 5 of the drawings, there is shown a first embodiment of an assembly 10 according to the present invention which comprises a rhythm control device 12 and a catheter 14. The assembly 10 is adapted to be implanted in a human body (not shown) with a portion of the catheter 14 inserted into a heart 16 (see FIG. 1) within the body.

Generally, the rhythm control device 12 comprises a housing 18 which contains electronic circuitry 20 (FIG. 5) including logic analyzing means 22 for analyzing electrical signals of the type produced by the heart 16 received through electrical connection means 24, for identifying signals indicating the onset of arrhythmia in the heart 16, and can provide electrical energy to the heart through the electrical connection means 24 to pace the heart 16 in response to a signal from the analyzing means 22 indication a predetermined condition in the heart 16; and supply means 26 within the housing 18 having an output port 28 for supplying under pressure through the outlet opening 30 a liquid chemical capable of treating the tissues of the heart 16 in response to a signal from the analyzing means 22 indicating the onset of arrhythmia of the heart 16.

Figure 2:
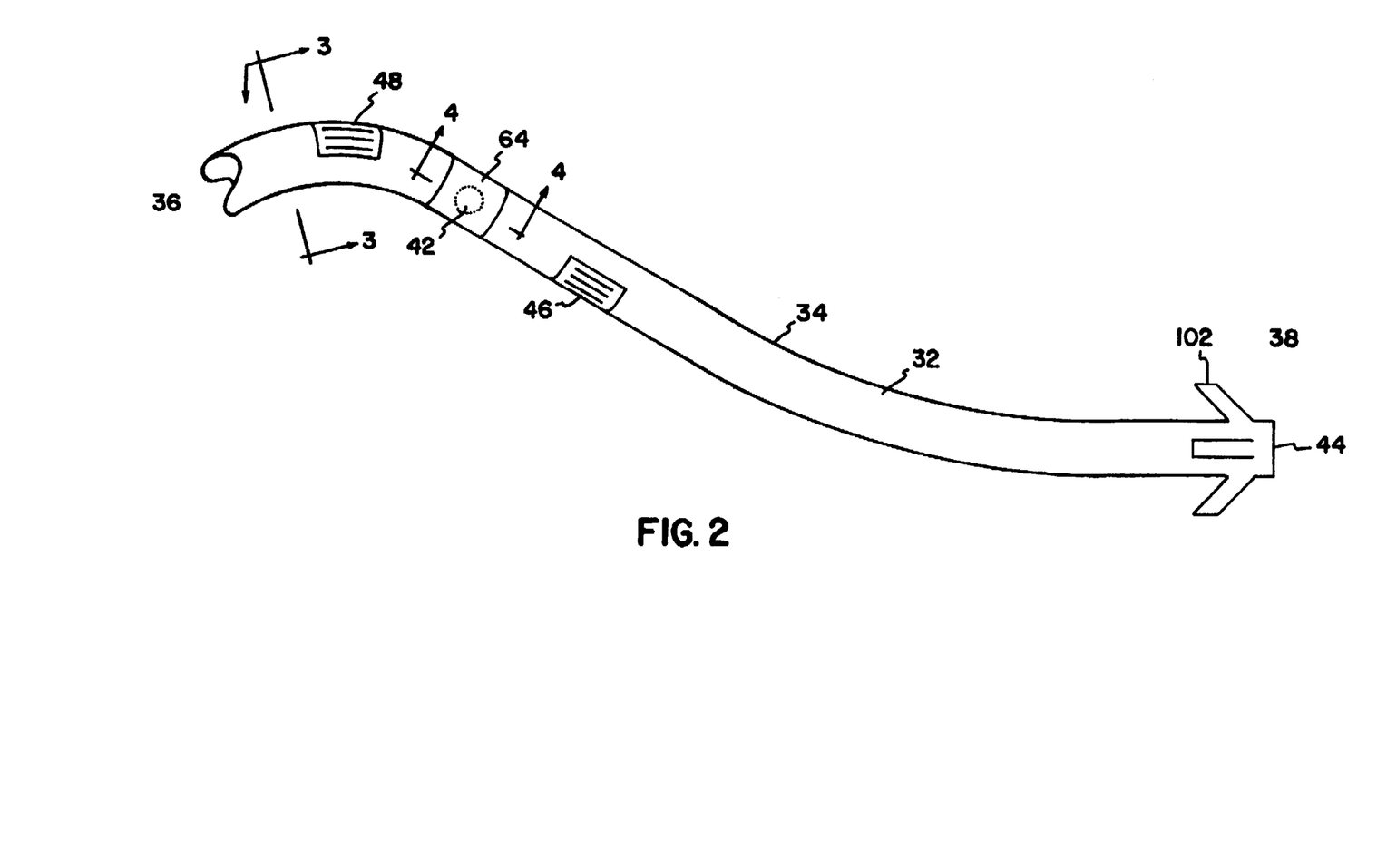
FIG. 2 is an enlarged fragmentary view of an end portion of the catheter of FIG. 1.

The catheter 14 comprises an elongate body 32 having a peripheral surface 34, proximal and distal ends 36 and 38 respectively, and a liquid lumen 40 (see FIGS. 3 and 4) extending longitudinally in the elongated body 32 from an inlet end at its proximal end 36 to an outlet port 42 between its proximal and distal ends 36 and 38. First, second, and third electrically conductive electrodes 44, 46, and 48 are attached on the peripheral surface 34 of the elongated body 32. As can be seen in FIG. 2, the first electrode 44 is a blunt tip electrode at the distal end 38, whereas the second and third electrodes 46 and 48 are semi-cylindrical electrodes partially encircling and disposed on opposite sides of the peripheral surface 34 of the elongated body 32 and on opposite sides of the outlet port 42.

Figure 1:
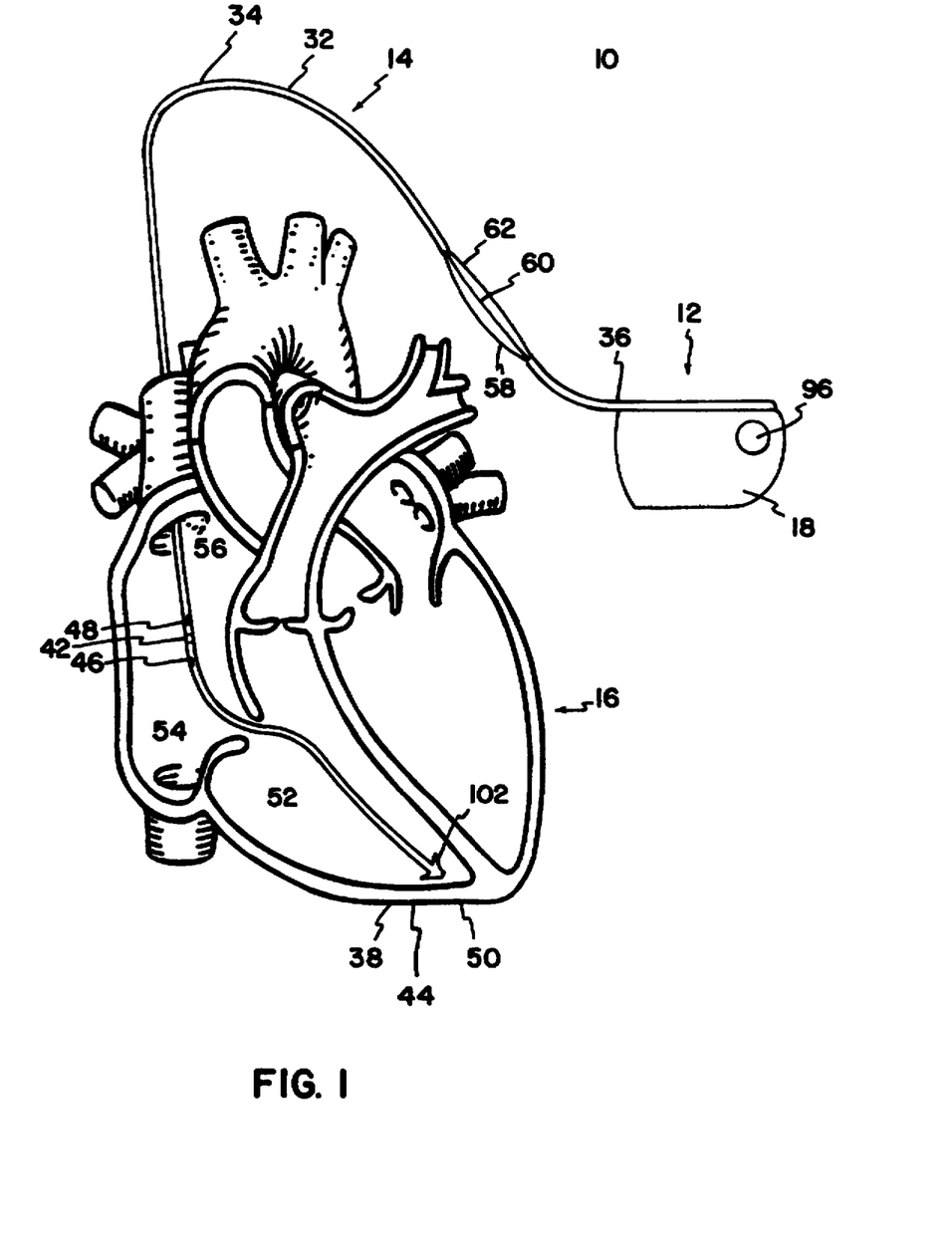
FIG. 1 is a side view of the present invention shown with a portion of the catheter inserted into a human heart from which portions have been removed to show details.

Alternatively, the outlet port 42 can be placed proximal to the third electrode 48, or distal to the second electrode 46. The second and third electrodes 46 and 48 are spaced apart (i.e., in the range of 5 to 20 millimeters) and are spaced longitudinally along the peripheral surface 34 from the distal end 38 by distances (i.e., in the range of 11 to 16 centimeters) that afford positioning the catheter 14 in the heart 16 with the first electrode 44 in the apex 50 of its right ventricle chamber 52 and the second and third electrodes in its right atrium chamber 54 as is illustrated in FIG. 1, or with the second and third electrodes in the superior vena cava vein 56 of the heart 16 that is connected with the right atrium chamber 54. First, second, and third electrical leads 58, 60 and 62 extend longitudinally within the elongated body 32 from contact ends (not shown) at its proximal end 36 to the first, second, and third electrodes 44, 46 and 48, respectively. The outlet port 42 is spaced longitudinally along the peripheral surface 34 from the distal end 38 by distances (i.e., in the range of 5 to 25 centimeters, preferably at a distance of 12 centimeters) that, as illustrated, afford positioning the catheter 14 in the heart 16 with the first electrode 44 in the apex 50 of the right ventricle chamber 52 and the outlet port 42 in the right atrium chamber 54 as illustrated in FIG. 1, or in the superior vena cava vein 56 that is connected with the right atrium chamber 54. Now referring to FIG. 4 valve means 64 on the elongate body 32 at the outlet port 42 afford movement of liquid under pressure in the liquid lumen 40 out through the outlet port 42 and prevent movement of liquid or blood around the peripheral surface 34 of the elongated body 32 into the outlet port 42.

The proximal end 36 of the catheter 14 is releasably attached to the medical device 12 with the inlet opening of the liquid lumen 40 in communication with the outlet opening 30 of the medical device 12 (not shown) and the contact ends of the electrical leads 58, 60 and 62 in electrical connection with electrical input connections 66, 68, and 70 (not shown) for the electronic means 20 so that the electronic means 20 receives bipolar signals from the right atrium chamber 54 of the heart 16 between the second and third electrodes 46 and 48 and unipolar signals from the right ventricle chamber 52 of the heart 16 between the first electrode 44 and the housing 18.

Figure 5:
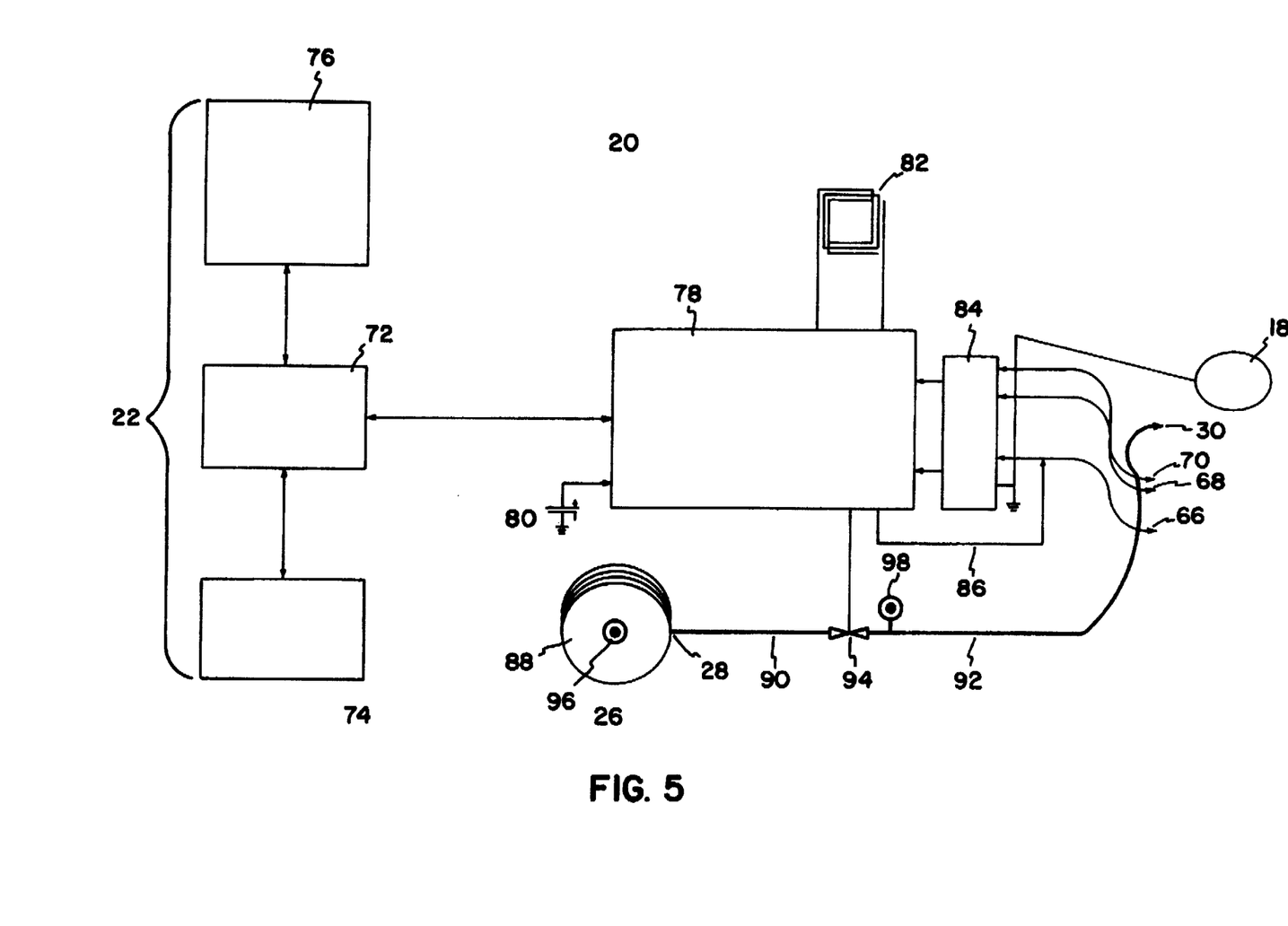
FIG. 5 is a schematic view of electronic circuitry and the drug reservoir.

Now referring to FIG. 5, analyzing means 22 for analyzing electrical signals of the type produced by the heart 16 received through electrical connection means 24, for identifying signals indicating the onset of arrhythmia in the heart 16, and can provide electrical energy to the heart through the electrical connection means 24 to pace the heart 16 in response to a signal from the analyzing means 22 indicating a predetermined condition in the heart 16 comprises a microcomputer 72 to which is coupled a program memory 74 that stores the control program that analyzes signals from the heart 16 to determine arrhythmia of the heart 16 and determines when to supply electrical energy to the heart through the electrical connection means 24 to effect sinus rhythm of the heart, and a read/write memory 76 that is programmable to afford setting of parameters, and which stores history of electrical impulses received from the heart. The microcomputer 72 is coupled to custom analog and digital circuitry 78 through which power is supplied by a depletable power supply or battery 80 and through which it is connected to a telemetry antenna 82 through which signals are provided to or received from the read/write memory 76. The electrical input connections 66, 68, and 70 are connected to the custom analog and digital circuitry 78 through filters and high voltage protection circuits 84 that protect the electronic means 20 from destructive electrical inputs such as could result from defibrillation of the heart by electrical impulses. A line 86 through which the electronic means can provide electrical energy to the heart to effect sinus rhythm of the heart 16 is connected around the filters and high voltage protection circuits 84 between the custom analog and digital circuitry 78 and the electrical input connection 66. Such electrical energy to the heart 16 paces the heart 16 in a unipolar modality.

The supply means 26 within the housing 18 having an outlet port 28 for supplying under pressure through the outlet opening 30 a liquid chemical capable of treating the tissues of the heart 16 in response to a signal from the analyzing means 22 indicating the onset of arrhythmia of the heart 16 comprises a pressurized chamber 88 (i.e., a container divided by a flexible diaphragm, one side of which is stored an inert gas under pressure, and on the other side of which is stored the liquid chemical). The liquid containing portion of the pressurized chamber is connected by lines 90 and 92 through a valve 94 to the outlet opening 30 which is coupled to the inlet opening of the liquid lumen 40 of the catheter 14. The valve is controlled between open and closed conditions by the microcomputer 72 with the custom analog and digital circuitry 78. The pressurized chamber is adapted to be filled through the use of a self-sealing septum 96 or other coupling means on the housing 18 of the medical device 12. The septum 96 may be constructed from any flexible polymer material including silicon rubber. A flush port 98 is connected to the line 92, and can be used to purge the liquid lumen 40 of the catheter 14. The housing 18 of the medical device 12 is constructed of bio-compatible materials, such as titanium, or 316 stainless steel.

Figure 4:
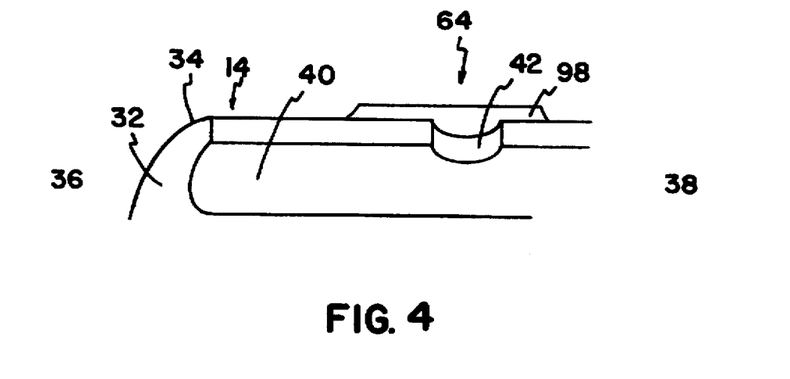
FIG. 4 is an enlarged cross sectional view taken approximately along lines 4—4 of FIG. 2.

Referring to FIG. 4, the valve means 64 at the outlet port 42 is provided by a cylindrical band 98 of resiliently elastic material tensioned around and fixed to the elongated body 32 along one edge so that the cylindrical band 98 extends over the outlet port 42. The cylindrical band 98 is adapted to be resiliently flexed by pressure applied thought the liquid in the lumen 40 to afford movement of liquid through the outlet port 42 and between the elongated body 32 and the cylindrical band 98. The cylindrical band 98 may be constructed from a variety of rubber materials such as silicone rubber or polyurethane.

Liquid chemicals capable of treating the tissues of the heart 16 that can be dispensed by the assembly 10 include, but are not limited to, quinine, disopyramide, procainamide, lidocaine, mexiletine, encainide, flecainide, propafenone, propanolol, nadolol, metrorolol, atenolol, amiodarone, sotalol, clofilium, dofetilide, ibutilide, verapamil, and diltiazem.

As can be seen from FIG. 1 the catheter 14 is releasably attached to and can be separated from the medical device 12 facilitate inserting it into the heart 16 of the human body. The catheter 14 is inserted into the heart 16 transvenously through a cephalic or subclavian vein (not shown) to position its distal tip 38 at the apex 50 of the right ventricle 52. The proximal end 36 of the catheter 14 is then attached to the medical device 12. The proximal end 36 of the catheter 14 and a portion of the medical device 12 are adapted to seal together to thereby both engage the contact ends on the electrical leads 58, 60, and 62 with the electrical input connections 66, 68, and 70 of the medical device 12 and couple the inlet opening to the liquid lumen 40 in the catheter 14 with the outlet opening 30 of the medical device 12. The medical device 12 of the attached assembly 10 is then positioned subcutaneously within the human body.

The elongated body 32 of the catheter 14 can be made by extrusion of an implantable polyurethane, silicone rubber or other implantable flexible bio-compatible polymer. The length of the elongated body 32 of the catheter 14 between the proximal and distal ends 36 and 38 is preferably in the range of 55 to 100 centimeters. The electrical leads 58, 60, and 62 can be made of MP35N alloy, or other commonly used electrical lead metal. The electrodes 44, 46 and 48 can be made of implantable metal such as platinum/iridium alloys, or other commonly used electrode metal (e.g., stainless steel).

Figure 3:
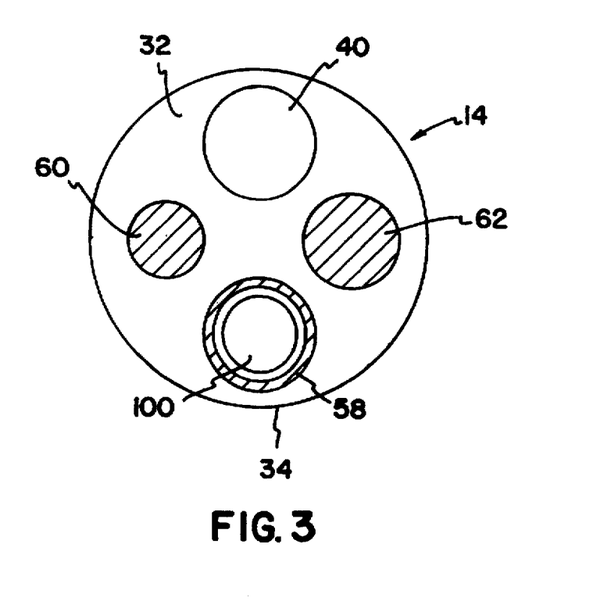
FIG. 3 is an enlarged cross sectional view taken approximately along lines 3—3 of FIG. 2.

The catheter 14 has a stylet passageway 100 (as depicted in FIG. 3) extending longitudinally in the elongated body 32 from an inlet end (not shown) located at the proximal end 36 to the distal tip. The stylet passageway 100 is adapted to receive a guide stylet for stiffening and shaping the catheter 14 during insertion of the catheter 14 into the heart 16.

The assembly includes means for securing the elongated body 32 within the heart 16. The elongated body 32 includes four circumferentially spaced tines 102 (see FIG. 2) near the distal end 38 of the catheter 14 that project both radially away from the periphery of the elongated body 32 and toward its proximal end 36. The tines afford passive fixation of the distal end 38 in the apex of the right ventricle 50 by engaging with the endocardial surface of the heart 16. Alternatively, the electrode 44 could include a helical corkscrew like projection adapted to be screwed into the tissue of the right ventricle 52 by rotating the elongated body 32 after its insertion into the heart 16 to anchor the catheter 14 in the heart 16 tissues.

Figures 6, 7:
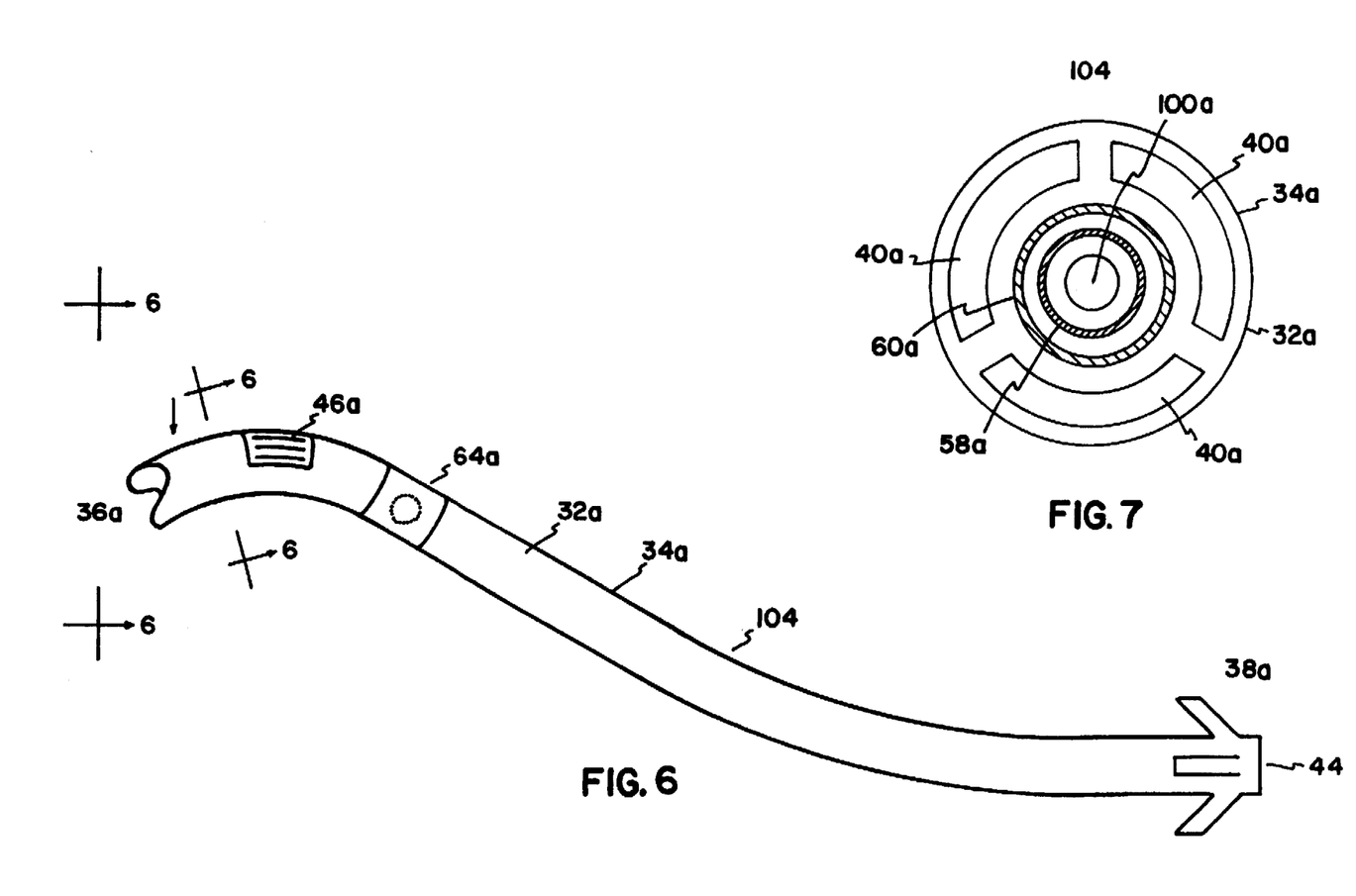
FIG. 6 is a fragmentary view of an end portion of a second embodiment of a catheter that can be used in an assembly of a medical device and catheter according to the present invention.
FIG. 7 is an enlarged cross sectional view taken approximately along lines 6—6 of FIG. 6.

Referring now to FIGS. 6 and 7 there is illustrated a second embodiment of a catheter 104 that can be used in an assembly of a medical device and catheter according to the present invention. The catheter 104 has portions that are similar in structure to the described above for the catheter 14, which portions have been identified by the same reference numerals to which have been added the suffix "a".

The catheter 104 has structural features and dimensions similar to catheter 14 and functions in essentially the same manner. The catheter 104 includes an elongate body 32a having a peripheral surface 34a, proximal and distal ends 36a and 38a respectively, and a liquid lumen 40a extending longitudinally in the elongated body 32a from an inlet end at its proximal end 36a to an outlet port and valve 64a between its proximal and distal ends 36a and 38a. The catheter 104, however, does not include the electrode 48 or the electrical lead 62 of the catheter 14.

Referring to FIG. 7, while the catheter could look similar to that of FIG. 3 with the electrical lead 62 removed, FIG. 7 shows an alternative configuration wherein the stylet passageway 100a forms a central lumen of the elongated body 32a and the electrical leads 58a and 60a are constructed of flexible wires which are arranged concentric with the central stylet passageway lumen 100a. The liquid lumen is formed by adjacent arcuate passageways 40a. The second electrode 46a of the catheter 104 is spaced longitudinally along its peripheral surface 34a from its distal end 38a by distances in the range of 11 to 16 centimeters, to afford positioning the catheter 104 in the heart 16 (not shown) with the first electrode 44a in the apex of the right ventricle chamber and the second electrode 46a in the right atrium chamber or in a major vein (i.e., the superior vena cava) of the heart connected with the right atrium chamber. Sensing in the right atrium 54 is unipolar between the electrode 46a and the housing 18 of the medical device 12. Sensing in the right ventricle 52 is unipolar between the electrode 44a and the housing 18 of the medical device 12. Unipolar pacing electrical energy can be provided to the heart through the first electrode 44a.

Figures 8, 9:
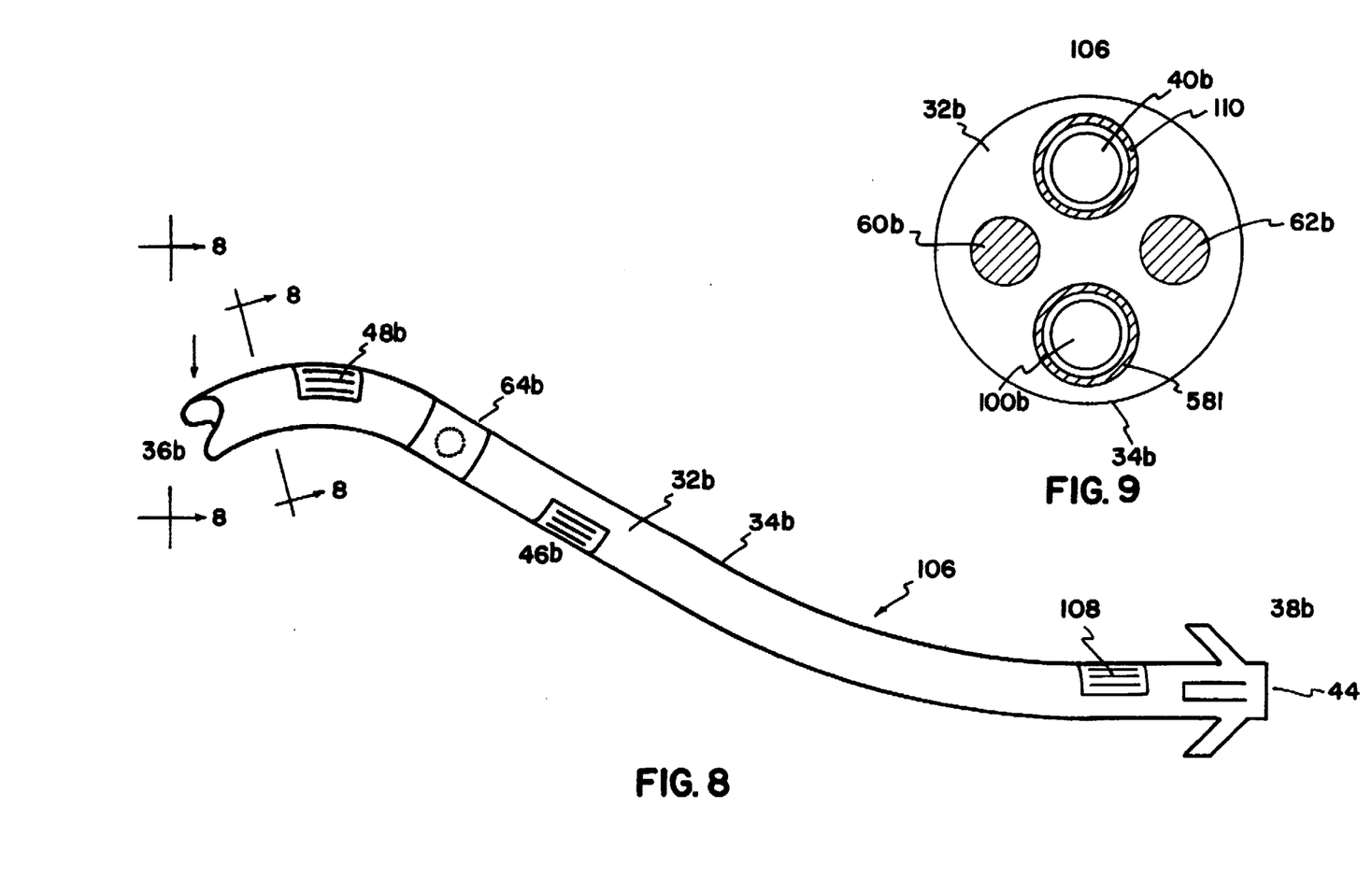
FIG. 8 is a fragmentary view of an end portion of a third embodiment of a catheter that can be used in an assembly of a medical device and catheter according to the present invention.
FIG. 9 is an enlarged cross sectional view taken approximately along lines 8—8 of FIG. 8.

Referring now to FIGS. 8 and 9 there is illustrated a third embodiment of a catheter 106 that can be used in an assembly of a medical device and catheter according to the present invention. The catheter 106 has portions that are similar in structure to the described above for the catheter 14, which portions have been identified by the same reference numerals to which have been added the suffix "b".

The catheter 106 has structural features and dimensions similar to catheter 14 and functions essentially in the same manner. The catheter 106 includes an elongate body 32b having a peripheral surface 34b, proximal and distal ends 36b and 38b, and a liquid lumen 40b extending longitudinally in the elongated body 32b from an inlet end at its proximal end 36b to an outlet port and valve 64b between its proximal and distal ends 36b and 38b. The catheter 106 includes a fourth electrode 108 and electrical lead 110 that are not provided on the catheter 14. The fourth electrode 108 is spaced longitudinally along the peripheral surface 34b from the distal end 38b by distances in the range of 5 to 20 millimeters, to afford positioning the catheter 106 in the heart (not shown) with the first and fourth electrodes 44b and 108 in the apex of the right ventricle chamber and the second and third electrodes 46b and 48b in the right atrium chamber or in a major vein (i.e., the superior vena cava) of the heart connected with the right atrium chamber. Sensing is bipolar between the electrodes 46b and 48b in the right atrium and bipolar between the electrodes 44b and 108 in the right ventricle. Bipolar or unipolar pacing electrical energy is provided to the heart through the first electrode 44b.

As another embodiment, electrodes 46, 48, and 108 may be cylindrical encircling the peripheral surface 34 of the elongated body 32.

The present invention has now been described with reference to specific embodiments thereof. It will be apparent to those skilled in the art that many changes and modifications can be made in the embodiments described without departing from the scope of the present invention.

We claim:

1. A catheter for use with a rhythm control device comprising:

an elongate body having a peripheral surface and having proximal and distal ends and having at least one liquid lumen extending longitudinally in said body from an inlet end at said proximal end to an outlet port between said proximal and distal ends;

first and second electrodes on said peripheral surface, said first electrode being at or adjacent to said distal end, said second electrode being spaced longitudinally along said peripheral surface from said distal end to afford positioning the catheter in the heart with said first electrode in the apex of the right ventricle chamber and said second electrode in one of the right atrium chamber or a major vein of the heart coupled to the right atrium chamber;

a first electrical lead extending longitudinally within said body from a contact end at said proximal end to said first electrode, and a second electrical lead extending longitudinally within said body from a contact end at said proximal end to said second electrode;

a valve on said body at said outlet port for affording movement of liquid under pressure in said liquid lumen out through said outlet port and for preventing movement of liquid around said peripheral surface into said outlet port; and connector means adapted for attaching the proximal end of said elongate body to the housing of a rhythm control device with said inlet opening of said liquid lumen in communication with the outlet port, the contact ends of said electrical leads in electrical connection with said connection means so that the rhythm control device receives signals through said first, and second electrodes, and the electrical energy to the heart is provided through said first electrode.

2. A catheter according to claim 1 further including:

a third electrode on said peripheral surface;

a third electrical lead extending longitudinally within said body from a contact end at said proximal end to said third electrode;

said third electrode being spaced longitudinally along said peripheral surface from said first and second electrodes to afford positioning the catheter in the heart with said first electrode in the apex of the right ventricle chamber and said second and third electrodes in one of the right atrium chamber or a major vein of the heart connected to the right atrium chamber;

said contact ends of said electrical leads being adapted for electrical connection with said connection means so that the rhythm control device receives signals between said second and third electrodes.

3. A catheter according to claim 1 further including:

third and fourth electrodes on said peripheral surface and third and fourth electrical leads extending longitudinally within said body from contact ends at said proximal end to said third, and fourth electrodes;

said third, and fourth electrodes being spaced longitudinally along said peripheral surface from each other and from said first and second electrodes to afford positioning said catheter in the heart with said first electrode in the apex of the right ventricle chamber;

said fourth electrode in the right ventricle chamber, and said second and third electrodes proximate the right atrium chamber adjacent a major vein of the heart connected to the right atrium chamber;

said contact ends of said electrical leads being adapted for electrical connection with said connection means so that the rhythm control device receives signals from between said second and third electrodes and from between said first and fourth electrodes, and the electrical energy to the heart is provided through said first electrode or fourth electrode.

4. A catheter according to claim 1 wherein said outlet port of said liquid lumen opens through said peripheral surface at a position spaced longitudinally along said peripheral surface from said distal end of said body to afford positioning said catheter in the heart with said distal end of said body in the apex of the right ventricle chamber and said outlet port proximate said right atrium chamber adjacent a major vein of the heart connected to the right atrium chamber;

said valve means comprises an enclosure of resiliently elastic material tensioned around said periphery and fixed along said peripheral surface over said outlet port whereby said material is flexed by pressure applied through liquid in said lumen to dispense said liquid from said outlet port.

5. A catheter according to claim 1 wherein said elongate body has a stylet passageway extending longitudinally in said body from an inlet end at said proximal end, said stylet passageway being adapted to receive a stylet for stiffening and shaping the catheter during insertion of the catheter.

6. A catheter according to claim 1 further including means adapted for securing the body within the heart.

7. A catheter according to claim 6 wherein said means adapted for securing the body within the heart comprises electrically conductive means attached and electrically connected to said first electrode and adapted to be embedded in the tissues of the heart.

8. A catheter according to claim 6 wherein said means adapted for securing the body within the heart comprises means attached to said body adjacent said distal end adapted to engage with the tissues of the heart.

9. A catheter according to claim 1 wherein said electrodes are semi-annular and partially encircle the peripheral surface of the body.

10. A catheter according to claim 1 wherein the length of said body between said distal and proximal ends is in the range of about 55 to 100 centimeters.

* * * * *